United States Patent
Vats et al.

(10) Patent No.: US 9,700,530 B2
(45) Date of Patent: Jul. 11, 2017

(54) CAPSULE DOSAGE FORM OF METOPROLOL SUCCINATE

(71) Applicant: SUN PHARMACEUTICAL INDUSTRIES LIMITED, Mumbai, Maharashtra (IN)

(72) Inventors: Sandeep Kumar Vats, Sonipat (IN); Balaram Mondal, East Midnapore (IN); Kalaiselvan Ramaraju, Tiruchirappalli (IN); Romi Barat Singh, Benares (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/337,611

(22) Filed: Oct. 28, 2016

(65) Prior Publication Data
US 2017/0042837 A1 Feb. 16, 2017

Related U.S. Application Data

(63) Continuation-in-part of application No. 15/012,775, filed on Feb. 1, 2016, now Pat. No. 9,504,655, which is a continuation of application No. PCT/IB2015/055195, filed on Jul. 9, 2015.

(60) Provisional application No. 62/022,316, filed on Jul. 9, 2014.

(51) Int. Cl.
| | | |
|---|---|---|
| *A61K 31/138* | (2006.01) | |
| *A61K 9/48* | (2006.01) | |
| *A61J 3/07* | (2006.01) | |
| *A61K 9/50* | (2006.01) | |
| *A61K 9/00* | (2006.01) | |

(52) U.S. Cl.
CPC ............ *A61K 31/138* (2013.01); *A61J 3/071* (2013.01); *A61K 9/0056* (2013.01); *A61K 9/0095* (2013.01); *A61K 9/485* (2013.01); *A61K 9/4808* (2013.01); *A61K 9/4858* (2013.01); *A61K 9/4866* (2013.01); *A61K 9/5078* (2013.01); *A61K 9/5047* (2013.01)

(58) Field of Classification Search
None
See application file for complete search history.

(56) References Cited

U.S. PATENT DOCUMENTS

| | | | |
|---|---|---|---|
| 5,246,714 A | 9/1993 | Dahlinder et al. | 424/497 |
| 6,156,342 A | 12/2000 | Sriwongjanya et al. | 424/473 |
| 2008/0113031 A1* | 5/2008 | Moodley | A61K 9/5073 424/490 |

FOREIGN PATENT DOCUMENTS

| | | | | |
|---|---|---|---|---|
| IN | WO 2009087663 A2 * | 7/2009 | | A61K 9/2866 |
| WO | WO 2009/087663 | 7/2009 | | A61K 9/26 |

OTHER PUBLICATIONS

International Preliminary Report on Patentability for International Application No. PCT/IB2015/055195 issued by WIPO on Jan. 19, 2017.
Co-pending U.S. Appl. No. 15/465,926, filed Mar. 22, 2017.
Co-pending U.S. Appl. No. 15/012,775, filed Feb. 1, 2016.
Office Action for U.S. Appl. No. 15/012,775, issued by USPTO on Mar. 21, 2016.
Co-pending PCT Application No. PCT/IB2015/055195 filed Jul. 9, 2015.
International Search Report and Written Opinion for International Application No. PCT/IB2015/055195, issued by PCT on Nov. 2, 2015.

* cited by examiner

*Primary Examiner* — Robert A Wax
*Assistant Examiner* — Quanglong Truong

(57) ABSTRACT

This disclosure provides an extended-release capsule dosage form of metoprolol succinate in the form of coated discrete units, wherein said capsule dosage form is bioequivalent to the marketed Toprol-XL® tablet. The extended-release capsule dosage form comprising coated discrete units can be sprinkled onto food to ease administration to patients who have difficulty swallowing tablets or capsules.

14 Claims, No Drawings

CAPSULE DOSAGE FORM OF METOPROLOL SUCCINATE

CROSS-REFERENCE TO RELATED APPLICATIONS

This application is a continuation-in-part of U.S. application Ser. No. 15/012,775 filed Feb. 1, 2016, which is a continuation of PCT Application No. PCT/IB2015/055195 filed Jul. 9, 2015, which claims the benefit of U.S. Provisional Application No. 62/022,316 filed Jul. 9, 2014.

FIELD OF THE INVENTION

The present invention provides an extended-release capsule dosage form of metoprolol succinate in the form of coated discrete units and processes for their preparation.

BACKGROUND OF THE INVENTION

Metoprolol is a beta-blocker that is prescribed for the treatment of hypertension, angina pectoris, and stable, symptomatic heart failure. Currently, the marketed extended-release dosage form of metoprolol succinate is a multiparticulate tablet dosage form comprising silicon dioxide beads as an inert core (Toprol-XL® tablet).

U.S. Pat. No. 5,246,714 discloses a controlled-release preparation containing a number of insoluble beads coated with one or more pharmaceutically active compounds. It further discloses examples of insoluble materials such as silicon dioxide, glass, or plastic resin particles.

In 2014, many generic metoprolol succinate extended-release tablets comprising multiparticulates were recalled from the U.S. market. As per the FDA Enforcement Reports, these tablets were recalled due to failed dissolution tests.

Compression of multiparticulates into a tablet dosage form is a challenging task. An additional 30% to 60% of tableting excipients are necessary to avoid any damage to the polymer coat and to retain the functional properties of the coat during compression. However, even after the process and excipient optimizations, cracks in the extended-release polymer coat are observed at the commercial scale. These cracks in the extended-release polymer coat impact the dissolution profile of the dosage form.

A capsule dosage form of coated multiparticulates offers an advantage over the tablet dosage form, as there is no compression step involved in capsule dosage forms. Further, this dosage form is easier to swallow and requires the addition of fewer excipients than the tablet dosage form.

Therefore, there is a need in the art to prepare an alternate extended-release dosage form of metoprolol succinate which is bioequivalent to the marketed Toprol-XL® tablet.

SUMMARY OF THE INVENTION

The present invention provides an extended-release capsule dosage form of metoprolol succinate in the form of coated discrete units, wherein said capsule dosage form is bioequivalent to the marketed Toprol-XL® tablet. Moreover, the extended-release capsule dosage form comprising coated discrete units can be sprinkled onto food to ease administration to patients who have difficulty swallowing tablets or capsules, e.g., pediatric patients and geriatrics. Soft foods generally used have varying pH levels, for example pudding has an alkaline pH and apple sauce has an acidic pH. Therefore, the selection of the soft food becomes an important aspect in view of stability of the dosage form comprising a functional coating. Exposure in soft food for a longer time may also impact the coating integrity, and the drug may be released in a burst release manner and may result in adverse effects in patients.

Also, coated discrete units can be administered through a feeding tube in a long term care setting to critically ill patients. However, coated discrete units may be difficult to administer through a feeding tube as the discrete units may form aggregates of larger size and block the feeding tube. Also, the coated discrete units may stick on the walls of feeding tube.

The present invention provides coated discrete units which are capable of being administered through a feeding tube by dispersing in an aqueous media before administration. Also, surprisingly, we have found that coated discrete units can be sprinkled onto soft foods having a diverse pH range without impacting on the release profile or stability, hence providing a patient's convenience to choose any available soft food of their choice.

DETAILED DESCRIPTION OF THE INVENTION

A first aspect of the present invention provides an extended-release capsule dosage form of metoprolol succinate in the form of coated discrete units, wherein the capsule dosage form comprises metoprolol succinate in an amount of from about 30% to about 70% by total weight of the dosage form and is bioequivalent to the marketed Toprol-XL® tablet.

According to one embodiment of this aspect, the extended-release capsule dosage form is in the form of sprinkle capsules.

According to another embodiment of this aspect, the sprinkle capsule dosage form may be sprinkled onto soft food, for example, applesauce, yogurt, cottage cheese, custard, or pudding, at the time of administration.

According to another embodiment of this aspect, the extended-release capsule dosage form comprises coated discrete units having a $d_{90}$ value of about 0.2 mm to 2.5 mm.

According to another embodiment of this aspect, the extended-release capsule dosage form in the form of coated discrete units comprising:
 a) inert cores;
 b) a drug layer over the inert cores comprising metoprolol succinate; and
 c) an extended-release layer over the drug layer The term "extended-release" includes controlled-release, modified-release, and sustained-release. The capsule dosage form is stable and has a similar release profile as compared to Toprol-XL® tablets throughout the shelf life of the product. Metoprolol succinate may be present in an amount of from about 30% to about 70% by total weight of the dosage form. In particular, from about 40% to about 60% by total weight of the dosage form, wherein the capsule shell weight is not included in the total weight of the dosage form.

Metoprolol succinate of the present invention may be in racemic form or as a pure enantiomer. Further, metoprolol succinate may be present in the capsule dosage form in a strength of about from 25 mg to about 200 mg. Coated discrete units comprising metoprolol succinate in a strength of 25 mg/50 mg, 100 mg, and 200 mg may be filled into size 4, size 2, and size 0 hard gelatin capsules respectively.

The term "discrete units," as used herein, refers to a plurality of pellets, granules, minitablets, or beads.

Bioequivalence is established by comparing pharmacokinetic parameters, for example AUC and $C_{max}$, of the present invention with Toprol-XL® tablets in healthy human subjects.

The term "AUC" refers to the area under the time/plasma concentration curve after the administration of the metoprolol succinate extended-release dosage form to healthy human subjects.

The term "$C_{max}$" refers to the maximum concentration of metoprolol in the blood following the administration of the metoprolol succinate extended-release dosage form to healthy human subjects.

The extended-release capsule dosage forms of metoprolol succinate are stable when subjected to stability conditions of 40° C. and 75% Relative Humidity (RH) for 6 months. Further, the coated discrete units are stable when sprinkled onto soft foods of different pH levels for at least 60 minutes. Also, the dispersion of the coated discrete units in an aqueous media is stable when administered in a feeding tube after holding for at least 10 minutes.

Inert cores may be selected from the group comprising of water-soluble or water-swellable.

According to another embodiment of this aspect, water-soluble or water-swellable inert cores are made up of sugar, microcrystalline cellulose, cellulose, starch, modified starch, or mixtures thereof.

According to another embodiment of this aspect, the inert core is a sugar core wherein said sugar is selected from the group consisting of glucose, mannitol, lactose, xylitol, dextrose, and sucrose.

Coated discrete units may be prepared by coating a drug layer comprising metoprolol succinate, optionally along with other pharmaceutically acceptable excipients, onto an inert core. Optionally, a seal coat layer may be present between the inert core and the drug layer. The seal coat may further comprise film-forming polymers. Further, the drug-layer coated cores are coated with an extended-release layer.

According to another embodiment of this aspect, the extended-release layer comprises a water-soluble/swellable polymer, a water-insoluble polymer, or mixtures thereof. The extended-release layer is present in an amount of from 5% to 30% based on the weight of the drug-layer coated cores.

Water-soluble/swellable polymers include hydroxypropyl methylcellulose having an apparent viscosity ranging from 100 cP to 150,000 cP (2% in water at 20° C.), e.g., K100, K4M, K15M, K100M, E4M, and E10M; hydroxypropyl cellulose, e.g., HPC-H, HPC-M, HPC-HF, and HPC-HXF; polyethylene glycol (molecular weight of about 3000 or above); poly(ethylene oxide), e.g., PEO-27, PEO-18, PEO-15, PEO-8, PEO-4, Polyox® WSR-1105, and Polyox® WSR-303; hydroxyethyl cellulose; carboxymethyl cellulose; xanthan gum; polyvinyl pyrrolidone; starch; and mixtures thereof.

Water-insoluble polymers include cellulose ethers, e.g., ethyl cellulose; cellulose esters, e.g., cellulose acetate; polymethacrylic acid esters copolymers, e.g., Eudragit® NE 30 D, and Eudragit® NE 40 D; aminoalkyl methacrylate copolymers, e.g., Eudragit® RL 100, Eudragit® RL PO, Eudragit® RS PO, and Eudragit® RS 100; copolymers of polyvinyl acetate and polyvinyl pyrrolidone, e.g., Kollidon® SR; and mixtures thereof. In particular, the extended-release polymer is a water-insoluble polymer. More particularly, the water-insoluble polymer is ethyl cellulose.

The extended-release polymer may be present in an amount of from 50% to 99% based on the weight of the extended-release layer.

According to another embodiment of this aspect, the extended-release layer comprises a water-insoluble polymer.

The extended-release layer comprising a water-insoluble polymer further comprises a pore-former selected from the group comprising low viscosity grade hydroxypropyl methylcellulose having an apparent viscosity of less than 100 cP (2% in water at 20° C.), e.g., K3, E5, E15, and E50; sodium alginate; sugars and sugar alcohols, e.g., sucrose, dextrose, lactose, maltitol, and lactitol; low molecular weight polyethylene glycol (molecular weight of less than 3000); polyvinyl alcohol; polyvinyl pyrrolidone; hydroxypropyl cellulose; and mixtures thereof. Pore-formers may be present in an amount of from 0% to 60% based on the weight of the extended-release layer.

According to another embodiment of this aspect, the extended-release layer comprises a mixture of ethyl cellulose and hydroxypropyl methylcellulose.

A second aspect of the present invention provides a process of preparation of an extended-release capsule dosage form of metoprolol succinate in the form of coated discrete units wherein the process comprises:
a) coating inert cores with a solution or dispersion of metoprolol succinate to obtain drug-layer coated cores;
b) coating the drug-layer coated cores of step a) with a solution or dispersion of an extended-release polymer; and
c) filling the extended-release cores of step b) into suitable size capsules.

A third aspect of the present invention provides an extended-release capsule dosage form of metoprolol succinate comprising coated discrete units having $d_{90}$ value between about 0.2 mm and 1.5 mm, wherein the coated discrete units, after dispersing in an aqueous media for at least 10 minutes, have a desired flowability when passed through a feeding tube, and contain not more than 0.5% by weight of the related substances.

According to one embodiment of this aspect, the coated discrete units have $d_{90}$ value of from about 0.2 mm to 1.2 mm.

According to another embodiment of this aspect, the particle size of the coated discrete units does not change more than 30% when exposed to aqueous media for at least 10 minutes. This is an important aspect, as swelling of the particles can lead to clogging of the feeding tube.

The term "$d_{90}$ value" as used herein means that 90% of the coated particles have a volume diameter in the specified range when measured by a light scattering method such as a Malvern® Mastersizer®.

According to another embodiment of this aspect, the desired flowability is defined as no clogging or aggregation is observed while the dispersion flows through the feeding tube.

A fourth aspect of the present invention provides an extended-release capsule dosage form of metoprolol succinate comprising coated discrete units having $d_{90}$ value between about 0.2 mm and 1.2 mm, wherein the coated discrete units, after being dispersed in an aqueous media and delivered through a feeding tube size NLT 10 F, at least 85% of metoprolol succinate was recovered at the exit of the feeding tube after holding for 10 minutes.

According to one embodiment of this aspect, the coated discrete units are in the form of plurality of pellets, granules, minitablets, or beads.

According to another embodiment of this aspect, the coated discrete units are lubricated before filling into the capsule.

According to another embodiment of this aspect, the lubricant is selected from the group consisting of colloidal silicon dioxide, stearic acid, magnesium stearate, calcium stearate, talc, hydrogenated castor oil, sucrose esters of fatty acid, microcrystalline wax, yellow beeswax, white beeswax, and mixtures thereof.

According to another embodiment of this aspect, the lubricant is present in an amount of from 0.001% to 5% by weight.

According to another embodiment of this aspect, the coated discrete units are administered by a feeding tube selected from the group consisting of NG tube, G tube, and J tube, wherein the NG tube is a size 5-18 F, the G-tube is a size 14-28 F, and the J tube is a size of 14-18 F.

According to another embodiment of this aspect, the coated discrete units are dispersed in an aqueous media in a latex-free syringe and subsequently delivered in a feeding tube.

A fifth aspect of the present invention provides an extended-release capsule dosage form of metoprolol succinate comprising coated discrete units, wherein the coated discrete units, when sprinkled on soft foods having different pH levels and exposed for at least 60 minutes, contains not more than 0.5% by weight of total related substances of metoprolol succinate.

A sixth aspect of the present invention provides an extended-release capsule dosage form of metoprolol succinate comprising coated discrete units with a $d_{90}$ value between about 0.2 mm and 1.5 mm when sprinkled on the soft foods, wherein a similar dissolution profile of metoprolol succinate is produced before and after exposure for at least 60 minutes to soft foods having different pH levels.

According to one embodiment of this aspect, the soft food is selected from the group consisting of pudding, apple sauce, cottage cheese, yogurt, ice cream, and custard.

According to another embodiment of this aspect, the dissolution profile is similar when the F2 value is more than 50 between the initial and after exposure.

A seventh aspect of the present invention provides an extended-release capsule dosage form of metoprolol succinate comprising coated discrete units having a $d_{90}$ value between about 0.2 mm and 1.5 mm, wherein the coated discrete units comprising 25 mg of metoprolol succinate are filled into a capsule that is size 3 or smaller.

According to one embodiment of this aspect, the coated discrete units are filled into a capsule that is size 4.

According to another embodiment of this aspect, the coated discrete units have a bulk density of 0.5-0.9 g/cc.

The dosage form may further comprise other pharmaceutically acceptable excipients.

Examples of pharmaceutically acceptable excipients include binders, diluents, lubricants/glidants, surfactants, and mixtures thereof.

Examples of binders include methyl cellulose, hydroxypropyl cellulose (HPC-L), carboxymethyl cellulose sodium, hydroxypropyl methylcellulose, polyvinylpyrrolidone, and mixtures thereof.

Examples of diluents include lactose, calcium carbonate, calcium phosphate, calcium sulfate, microcrystalline cellulose, cellulose powdered, fructose, lactitol, mannitol, sorbitol, starch, sucrose, and mixtures thereof.

Examples of lubricants or glidants include colloidal silicon dioxide, stearic acid, magnesium stearate, calcium stearate, talc, hydrogenated castor oil, sucrose esters of fatty acid, microcrystalline wax, yellow beeswax, white beeswax, and mixtures thereof.

Examples of surfactants include sodium lauryl sulfate, sodium dodecyl sulfate, ammonium lauryl sulfate, benzalkonium chloride, alkyl poly(ethylene oxide), copolymers of poly(ethylene oxide) and poly(propylene oxide), commercially known as poloxamers or poloxamines, polyvinyl alcohol (PVA), fatty alcohols, polyoxyethylene alkyl ether, polyoxyethylene alkylaryl ether, polyethylene glycol fatty acid ester, alkylene glycol fatty acid mono ester, sucrose fatty acid ester, sorbitol monolaurate (Span® 20 or Span® 80), polyoxyethylene sorbitan fatty acid ester (polysorbates), and mixtures thereof.

The coating of the present invention may further comprise excipients selected from the group comprising plasticizers, binders, opacifiers, anti-tacking agents, anti-foaming agents, colors, film-forming polymers, or mixtures thereof. Organic or aqueous solvents may be used during the coating process. Solvents may be selected from the group comprising water, acetone, isopropyl alcohol, ethanol, isopropyl acetate, methylene chloride, and mixtures thereof.

Examples of plasticizers include propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglyceride, cetyl alcohol, and mixtures thereof.

Examples of opacifiers include titanium dioxide, silicon dioxide, talc, calcium carbonate, behenic acid, and mixtures thereof.

Examples of anti-tacking agents include talc, colloidal silicon dioxide, and mixtures thereof.

Examples of anti-foaming agents include silicon based surfactants, e.g., simethicone; vegetable oils; waxes; hydrophobic silica; polyethylene glycol; and mixtures thereof.

Coloring agents may be selected from FDA-approved colorants such as iron oxide, lake of tartrazine, allura red, titanium dioxide, and mixtures thereof.

Examples of film-forming polymers include hydroxypropyl methylcellulose, methyl cellulose, carboxymethyl cellulose, hydroxyethyl cellulose, polyethylene glycol, polyvinyl alcohol, and mixtures thereof. Alternatively, commercially available coating compositions comprising film-forming polymers marketed under various trade names, such as Opadry®, may also be used for coating.

Coating may be carried out by using any conventional coating techniques known in the art, such as spray coating in a conventional coating pan, fluidized bed processor, or dry powder coating.

The following examples illustrate the invention but are not to be construed as limiting the scope of the invention.

EXAMPLES

| Ingredients | Example 1 Quantity/Capsule (mg) | Example 2 Quantity/Capsule (mg) | Example 3 Quantity/Capsule (mg) |
|---|---|---|---|
| Drug Layer | | | |
| Metoprolol succinate USP equivalent to 25 mg of Metoprolol Tartrate, USP | 23.750 | 95.000 | 190.000 |
| Opadry ® clear | 2.375 | 9.500 | 19.000 |
| Sugar spheres | 18.750 | 75.000 | 150.000 |
| Purified water | q.s. | q.s. | q.s. |
| Extended-Release | | | |

-continued

| Ingredients | Example 1 Quantity/Capsule (mg) | Example 2 Quantity/Capsule (mg) | Example 3 Quantity/Capsule (mg) |
|---|---|---|---|
| Layer | | | |
| Ethyl cellulose | 3.269 | 13.076 | 26.152 |
| Hydroxypropyl methylcellulose | 0.577 | 2.308 | 4.616 |
| Triethyl citrate | 0.096 | 0.384 | 0.768 |
| Isopropyl alcohol | q.s. | q.s. | q.s. |
| Talc | 0.096 | 0.384 | 0.768 |
| Purified water | q.s. | q.s. | q.s. |
| Lubrication | q.s. | q.s. | q.s. |
| Talc | 0.489 | 1.956 | 3.912 |

Manufacturing Process:

1) Metoprolol succinate and Opadry® clear were added to the purified water to form a dispersion.
2) The dispersion of step 1 was sprayed onto sugar spheres to form drug-coated cores.
3) Ethyl cellulose was dispersed in isopropyl alcohol and purified water.
4) Hydroxypropyl methylcellulose, talc, and triethyl citrate were added into the dispersion of step 3.
5) The dispersion of step 4 was sprayed onto the drug-coated cores of step 2 to form extended-release discrete units.
6) The extended-release discrete units of step 5 were lubricated with talc.
7) The lubricated extended-release discrete units of step 6 were filled into size 4 capsule shells.

Dissolution Studies:

Dissolution tests were carried out using capsules prepared in Example 1 and Toprol-XL® tablets.

The dissolution was carried out in a USP type II apparatus, paddle rotating at 50 RPM, at a temperature of 37° C.±0.5° C., in 500 mL of pH 7.5 phosphate buffer. The results of the dissolution tests are shown in Table 1.

TABLE 1

Dissolution profile of Example 1 and Toprol-XL® tablets

| Time (hrs) | % drug released (metoprolol succinate) in 500 ml of phosphate buffer | |
|---|---|---|
| | Toprol-XL® | Example 1 |
| 1 | 11 | 3 |
| 2 | 19 | 16 |
| 4 | 31 | 30 |
| 8 | 53 | 57 |
| 12 | 71 | 76 |
| 16 | 84 | 87 |
| 20 | 91 | 92 |

It is evident that Example 1 provides a release profile which is comparable to Toprol-XL® tablets.

Simulation Studies:

The pharmacokinetic profile ($C_{max}$ and AUC) of Example 1 was predicted using software Phoenix® 64 (WinNonlin® 6.4 & IVIVC toolkit 2.2). The predicted pharmacokinetic values of Example 1 were compared with pharmacokinetic values of Toprol-XL® tablet under fed and fasted conditions. Table 2 shows the simulated bioequivalence data of Example 1.

TABLE 2

Simulated T/R ratio for Example 1 with regard to Toprol-XL® tablets

| Parameter | Fed T/R Ratio | Fasted T/R Ratio |
|---|---|---|
| $AUC_{last}$ | 1.03 | 0.95 |
| $C_{max}$ | 1.03 | 1.09 |

From the above data, it is evident that the metoprolol extended release capsules of Example 1 would be bioequivalent to Toprol-XL® tablets under fed and fasted conditions.

In Vitro NG Tube Studies:

a) Recovery after Passing Through NG Tube:

A capsule of Example 3 was opened and coated discrete units having $d_{90}$ value$_{od}$ about 0.85 mm were dispersed in 50 mL of water in a latex-free syringe and was held for 60 minutes in a syringe. An NG tube (12 F) was attached to the latex-free syringe. Pressure was then applied to the syringe and the dispersion was transferred to the NG tube. Flowability and recovery of the coated discrete units upon exiting the NG tube were determined. No aggregation or sticking to the walls was observed. Table 3 shows that the desired amount of metoprolol succinate was recovered at the exit of the NG tube.

TABLE 3

Capsules of Example 3 were tested for recovery after passing through an NG tube

| | Control (before passing through NG tube) | Initial (0 min) | After holding for 60 min |
|---|---|---|---|
| Recovery (%) | 101.87 | 101.36 | 99.83 | b) Related Substance after Passing Through NG Tube:

A similar procedure was followed as given in the recovery test.

The related substance (RS) determination was carried out using HPLC method involving a Superspher® RP select B, 4 µm, 125 mm×4.0 mm column, and a mobile phase comprising a mixture of sodium dodecyl sulfate solution and acetonitrile in the ratio of 60:40 v/v. The initial and after-holding dispersions were analyzed for total related substances. The dispersion of coated discrete units in an aqueous media was found to be stable with regard to related substances in the NG tube, as given in Table 4.

TABLE 4

Capsules of Example 3 were tested for RS after passing through an NG tube

| | Initial (0 min) | After holding for 60 min |
|---|---|---|
| Total RS (% w/w) | 0.06 | 0.06 | c) Particle Size Determination

A Similar procedure was followed as given in the recovery test. The particle size of the units of Example 2 was determined using a Malvern® Mastersizer®. Table 5 shows that no significant change in particle size was observed after holding a coated unit dispersion for 60 minutes.

TABLE 5

Particle size of Example 2 was determined before and after passing through an NG tube

|  | Initial (0 min) | After holding for 60 min |
|---|---|---|
| $d_{90}$ (mm) | 0.85 | 0.85 |
| $d_{50}$ (mm) | 0.74 | 0.77 |
| $d_{10}$ (mm) | 0.63 | 0.67 |

In Vitro Soft Food Studies a) Related Substances

A capsule of Example 2 was opened and coated discrete units were tested for RS after exposure to applesauce for 60 minutes.

Related substance (RS) determination was carried out using HPLC method involving a Superspher® RP select B, 4 μm, 125 mm×4.0 mm column, and a mobile phase comprising a mixture of sodium dodecyl sulfate solution and acetonitrile in the ratio of 60:40 v/v. The coated discrete units were found to be stable in applesauce with regard to related substances as given in Table 6.

TABLE 6

RS of coated discrete units after exposure to applesauce

|  | Exposure time of 10 min | Exposure time of 60 min |
|---|---|---|
| Total RS (% w/w) | 0.10 | 0.10 | b) Assay

A capsule of Example 3 was opened and coated discrete units were tested for assay after exposure to various soft foods for 60 minutes. Assay determination was carried out using HPLC method involving column LiChrosorb® RP-8, 5 μm, 125 mm×4.0 mm, and a mobile phase comprising a mixture of sodium dodecyl sulfate solution and acetonitrile in the ratio of 60:40 v/v. The coated discrete units were found to be stable with regard to the assay as given in Table 7.

TABLE 7

Assay of coated discrete units after exposing to various soft foods

| Assay | Exposure time of 0 min | Exposure time of 60 min |
|---|---|---|
| Applesauce | 102.50 | 102.20 |
| Yogurt | 105.50 | 101.40 |
| Pudding | 103.20 | 103.50 | c) Dissolution Studies in Soft Food

The dissolution tests were carried out using capsules prepared in Example 3. A capsule was opened and the coated discrete units were placed into soft foods.

The dissolution was carried out in a USP type II apparatus, paddle rotating at 50 RPM, at a temperature of 37° C.±0.5° C., in 500 mL of pH 6.8 phosphate buffer. Table 8 shows that the dissolution profile of the coated discrete units is similar before and after exposure to various soft foods.

TABLE 8

Percentage drug release of an extended-release composition of metoprolol as per Example 3

| Time (hr) | Exposure time 0 min | Applesauce Exposure time 60 min | Yogurt Exposure time 60 min | Pudding Exposure time 60 min |
|---|---|---|---|---|
| 1 | 4 | 11 | 10 | 7 |
| 2 | 12 | 22 | 18 | 13 |
| 4 | 28 | 37 | 27 | 23 |
| 8 | 53 | 58 | 52 | 41 |
| 12 | 69 | 73 | 67 | 59 |
| 16 | 80 | 82 | 77 | 73 |
| 20 | 87 | 88 | 84 | 83 |
| 24 | 91 | 92 | 88 | 89 |
| F2 | 100 | 60 | 69 | 57 |

Based on the in vitro soft food studies, it was concluded that the stability, as well as dissolution of the product, is not impacted by soft foods having different pH levels.

We claim:

1. An extended-release capsule dosage form of metoprolol succinate comprising coated discrete units having a $d_{90}$ value between about 0.2 mm and 1.5 mm, wherein the coated discrete units, after dispersing in an aqueous media for at least 10 minutes, have a desired flowability when passed through a feeding tube and contain not more than 0.50% by weight of the related substances of metoprolol succinate.

2. The extended-release capsule dosage form according to claim 1, wherein the coated discrete units have $d_{90}$ value from about 0.2 mm to 1.2 mm.

3. The extended-release capsule dosage form according to claim 1, wherein the particle size of the coated discrete units does not change more than 30% when exposed to an aqueous media for at least 10 minutes.

4. An extended-release capsule dosage form of metoprolol succinate comprising coated discrete units have $d_{90}$ value between about 0.2 mm to 1.2 mm, wherein the coated discrete units when dispersed in aqueous media and delivered through a feeding tube having size NLT 10 F, at least 85% of metoprolol succinate is recovered at the exit of feeding tube after holding for at least 10 minutes.

5. The extended-release capsule dosage form according to claim 1, wherein the coated discrete units are in the form of a plurality of pellets, granules, minitablets, or beads.

6. The extended-release capsule dosage form according to claim 1, wherein the coated discrete units are lubricated before filling into the capsule.

7. The extended-release capsule dosage form according to claim 6, wherein the lubricant is selected from the group consisting of colloidal silicon dioxide, stearic acid, magnesium stearate, calcium stearate, talc, hydrogenated castor oil, sucrose esters of fatty acid, microcrystalline wax, yellow beeswax, white beeswax, and mixtures thereof.

8. The extended-release capsule dosage form according to claim 1, wherein the coated discrete units are administered by a feeding tube selected from the group consisting of NG tube, G tube, and J tube.

9. The extended-release capsule dosage form according to claim 8, wherein the coated discrete units are dispersed in an aqueous media in a latex-free syringe and subsequently delivered through a feeding tube.

10. An extended-release capsule dosage form of metoprolol succinate comprising coated discrete units having a $d_{90}$ value between about 0.2 mm and 1.5 mm, wherein the coated discrete units, when sprinkled on soft foods having different pH levels and exposed for at least 30 minutes, contain not more than 0.50% by weight of the total related substances of metoprolol succinate.

11. An extended-release capsule dosage form of metoprolol succinate comprising coated discrete units having a $d_{90}$ value between about 0.2 mm and 1.5 mm, which, when sprinkled onto soft foods, produces a dissolution profile of metoprolol succinate similar before and after exposure for at least 30 minutes to soft foods having different pH levels.

12. The extended-release capsule dosage form according to claim 4, wherein the coated discrete units are in the form of a plurality of pellets, granules, minitablets, or beads.

13. The extended-release capsule dosage form according to claim 4, wherein the coated discrete units are lubricated before filling into the capsule.

14. The extended-release capsule dosage form according to claim 4, wherein the coated discrete units are administered by a feeding tube selected from the group consisting of NG tube, G tube, and J tube.

* * * * *